United States Patent
Rosberg

(10) Patent No.: US 9,102,505 B2
(45) Date of Patent: Aug. 11, 2015

(54) BRIDGE CRANE ASSEMBLY AND A METHOD FOR INSTALLING THE SAME

(75) Inventor: Maria Rosberg, Helsinki (FI)

(73) Assignee: CALISTO OY, Helsinki (FI)

( * ) Notice: Subject to any disclaimer, the term of this patent is extended or adjusted under 35 U.S.C. 154(b) by 105 days.

(21) Appl. No.: 13/820,217

(22) PCT Filed: Apr. 3, 2012

(86) PCT No.: PCT/FI2012/050340
§ 371 (c)(1),
(2), (4) Date: Mar. 1, 2013

(87) PCT Pub. No.: WO2013/150172
PCT Pub. Date: Oct. 10, 2013

(65) Prior Publication Data
US 2014/0190919 A1    Jul. 10, 2014

(51) Int. Cl.
*B66C 23/18* (2006.01)
*B66C 17/06* (2006.01)
*B66C 19/02* (2006.01)

(52) U.S. Cl.
CPC ............... *B66C 17/06* (2013.01); *B66C 19/02* (2013.01); *B66C 23/18* (2013.01); *Y10T 29/49826* (2015.01)

(58) Field of Classification Search
USPC ......... 212/179, 175, 294, 312, 315, 324, 328, 212/336
See application file for complete search history.

(56) References Cited

U.S. PATENT DOCUMENTS

| 7,621,410 | B1 | 11/2009 | Updegrove et al. |
| 7,726,497 | B1 | 6/2010 | Updegrove et al. |
| 2012/0031868 | A1* | 2/2012 | Willim .................. 212/299 |

FOREIGN PATENT DOCUMENTS

| EP | 2196427 | 6/2010 | |
| JP | 04306366 A | * 10/1992 | ............. E04G 21/28 |

OTHER PUBLICATIONS

International Search Report, Dated Jan. 14, 2013, in PCT/FI2012/050340.

* cited by examiner

*Primary Examiner* — Sang Kim
*Assistant Examiner* — Juan Campos, Jr.
(74) *Attorney, Agent, or Firm* — Young & Thompson

(57) ABSTRACT

The invention relates to bridge crane assembly and a method for installation of a bridge crane. The invention is especially applicable for use in service and repair of vehicles and other heavy equipment in field conditions, such as crisis areas. The bridge crane assembly is supported by two containers (91, 92), upon which there are support frames (10, 20). The support frames are fixed to the top corners of the containers with twistlocks (19a-19d, 29a-29d), and the support frames support a crane bridge (30) with a hoist (40).

15 Claims, 5 Drawing Sheets

BRIDGE CRANE ASSEMBLY AND A METHOD FOR INSTALLING THE SAME

FIELD OF INVENTION

The invention relates to bridge crane assembly and a method for installation of a bridge crane. The invention is especially applicable for use in service and repair of vehicles and other heavy equipment in field conditions.

BACKGROUND TECHNOLOGY

In peace time depots and workshops there is a need for providing service, repair and maintenance of vehicles and other heavy equipment. In such activities it is often necessary to lift a powerpack, a weapon system or other heavy equipment. In a depot there is usually a permanently installed bridge crane for providing such lifting capacity. A bridge crane is thus a compulsory facility in a in order to provide the servicing, repair and maintenance work.

In field conditions, such as crisis areas, it is often not possible to have permanent bridge crane installations, as providing proper workshops in field conditions is not logistically and economically feasible. In such conditions the lifting is commonly done with a mobile crane. However, there are some problems related to this solution. There is a high investment and maintenance cost in using a mobile crane. It is also an expensive and dangerous procedure to transfer a mobile crane to a crisis area. If a mobile crane is available in a crisis area it is usually needed for other tasks as well, and the mobile crane may therefore not be available for the service and repair work. A mobile crane is also slow, inaccurate and not very stable compared to a bridge crane. A mobile crane also has no ballistic or mine protection and is therefore highly dangerous to move by driving to the destination from a main airport, for example. It also requires a trained person for using the mobile crane, whereby there is a risk that such a person is not always available when the mobile crane is needed. There is another known solution based on using armoured recovery vehicles for the lifting. However, this solution has some similar problems as using a mobile crane.

There is a further prior art solution of using a movable A-type bridge crane. However, such movable A-type bridge cranes are only suitable for plain, hard ground. If used on a soft or uneven ground there is a risk of overturning. Such movable A-type bridge cranes only move a load in vertical and transverse directions, they do not offer a possibility to move the load in longitudinal direction. They are usually also not designed for very heavy loads and have limited/restricted lifting capacity. A lifting capacity of several tons is desirable.

It is inevitable to have lifting capacity in order to provide e.g. required servicing for vehicles, among other required tasks. The insufficient lifting resources have a consequence that the vehicles and other heavy equipment are not serviced and repaired properly or maintained according to maintenance schedules. This may cause additional risks and additional life cycle costs in using the vehicles.

SUMMARY OF THE INVENTION

The object of the invention is to provide a bridge crane which can be used in field conditions, such as crisis areas, and by which the above problems of prior art are decreased or avoided. The bridge crane according to the invention is in effect an easily movable, non-permanent workshop for use in areas where providing a sufficient lifting capacity with permanently installed bridge crane(s) is not suitable, and where containers are available.

The object of the invention can be achieved with a bridge crane assembly, suitable for use in field conditions, such as crisis areas, comprising a hoist, at least one horizontal crane bridge supporting the hoist, and first and second support frame structures supporting the crane bridge(s) at both ends of the bridge(s) respectively, which is characterised in that the first support frame structure comprises means for fixing the first support frame structure to the top of a first container and the second support frame structure comprises means for fixing the second support frame structure to the top of a second container.

A method for installing a bridge crane is also provided, comprising phases in which
- a first support frame is fixed to the top corners of a first container,
- a second support frame is fixed to the top corners of a second container,
- a crane bridge is connected on and between the first and second support frames,
- a hoist is connected to the crane bridge.

Some preferable embodiments of the invention are described in the dependent claims.

In one embodiment of the invention the support frame is fixed to the top corners of the containers with twistlocks. The corners are the only points of attachment to be used on standard, inspected containers. Therefore, using the containers for the bridge crane assembly does not prevent the use of the containers for conventional shipping purposes afterwards.

In one embodiment of the invention the support frames comprise horizontal support beams supporting the hoist bridge, wherein the hoist bridge is arranged to be movable along said support beams.

In one embodiment of the invention the parts of the crane assembly can be transported in separate crates which fit into a standard 20 ft container.

In a further embodiment of the invention the bridge crane assembly comprises a tent for covering the other parts of the assembly and for protecting from environmental conditions.

In one embodiment of the invention the bridge crane assembly has an auxiliary crane for lifting and supporting the parts of the bridge crane assembly during installation.

It is possible to achieve significant advantages with the present invention. A container can be used for transporting other parts of the bridge crane assembly according to the invention, but it is also possible to transport the parts of the assembly by other means. It is inexpensive to transfer the light weight parts of a bridge crane assembly in crates into areas with low levels of infrastructure, and they can be further transported to the crisis area with helicopters. Transferring a bridge crane assembly with helicopters is safe compared to road transport in crisis areas, and no ballistic or mine protection is needed for the transport.

Since a lot of goods are transported to crisis areas in containers there are plenty of containers readily available. It is therefore easy to arrange a suitable amount of containers for supporting the bridge crane according to the invention. A container of a bridge crane assembly can also be used for other purposes when it is a part of the bridge crane assembly. It can be used as a storage for tools and miscellaneous equipment, for example.

A bridge crane assembly according to the invention can be assembled and disassembled in a very short time. It is not necessary to have more than two workers for assembling or disassembling the bridge crane. The investment and maintenance costs of the bridge crane assembly according to the invention are small compared to other solutions.

A bridge crane according to the invention is continuously available for lifting in its installation location. The bridge crane is very stable as it is supported by containers at both sides of the bridge crane. The containers are rigid and they can bear a high weight load. A bridge crane assembly according to the invention can have a suitable lifting capacity for the required lifting purposes. Good lifting safety and accuracy are achieved when the bridge crane has a fixed installation on containers. A container has a large bottom area, and it is therefore possible to install the bridge crane assembly even on soft ground, such as sand or clay. The support frame structure of the bridge crane extends above the containers. Based on the height of the container and the additional height provided by the support structure on the top of the containers, the bridge crane assembly has a suitable lifting height for said lifting purposes.

In this patent application a "container" means a shipping container according to the ISO 668 standard, or alike, which container is made of steel.

BRIEF DESCRIPTION OF DRAWINGS

In the following the invention is described with reference to the enclosed drawings, in which.

DETAILED DESCRIPTION OF PREFERRED EMBODIMENTS

Figure 1:
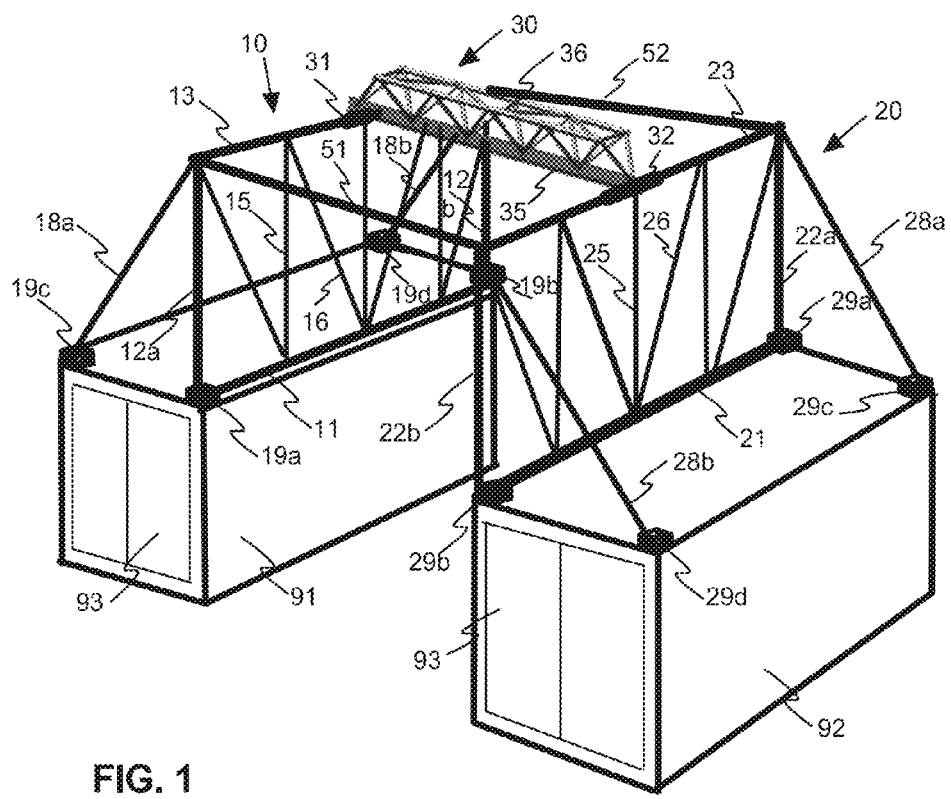
FIG. 1 illustrates an exemplary bridge crane assembly according to the invention as a perspective view.
Figure 2:
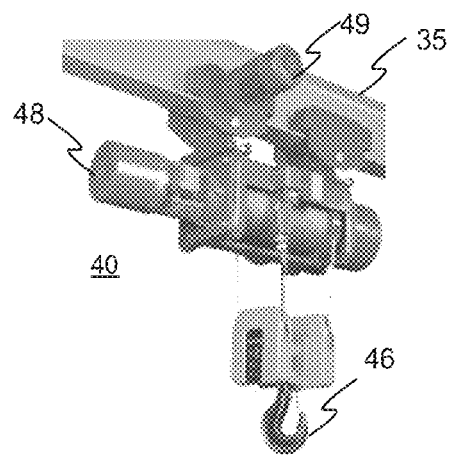
FIG. 2 illustrates an exemplary hoist of a bridge crane assembly according to the invention.

FIG. 1 illustrates perspective view of an exemplary bridge crane assembly according to the invention. An exemplary hoist of the assembly is illustrated in a separate FIG. 2. The assembly has two shipping containers 91 and 92. Such containers typically have doors 93 at their ends. The bridge crane assembly further has two support frames 10 and 20 on the top of the containers. The support frames support the crane bridge 30, which has a hoist 40.

The support frames 10 and 20 are symmetrically constructed. Therefore, one of the two support frames 10 is next described. The support frame 10 has a main frame which comprises a horizontal lower beam 11 and a horizontal upper beam 13. Two vertical beams 12a and 12b connect the horizontal beams to each other. The main frame is further supported by vertical support beams 15 and diagonal support beams 16 inside the rectangular main frame.

The main frame is fixed to the top front corners of the container 91. Twistlocks 19a and 19b are used for the attachment. There are also diagonal back support beams 18a and 18b, which are attached to the upper corners of the main frame and the back top corners of the container 91. The attachment of the back support beams to the container corners is accomplished using twistlocks 19c and 19d.

The second support frame 20 has corresponding parts 21-29 as the parts 11-19 of the first support frame, respectively.

The upper beams 13 and 23 of the support frames 10 and 20 are arranged to support the crane bridge 30. The crane bridge is connected to the support beams 13 and 23 with trolleys 31 and 32, which have rollers in order to allow longitudinal movement along the support beams 13 and 23. The longitudinal movement of the crane bridge can arranged manually or by motor(s). The support frames on top of each container are tied together by the top lateral supports 51 and 52 which keep the crane bridge end distance fixed for the length of the bridge crane and also provide stops to prevent the bridge crane from falling off the crane support frames.

The crane bridge 30 has an integral beam profile 35 for carrying a hoist 40. The crane bridge is of truss type construction The hoist may travel along the beam profile of the bridge in transversal direction. The movement may be arranged manually or by a motor 49. The hoist has a hook 46 for attachment to a load to be lifted. The lifting arrangement of the hoist may be manual or run by a motor 48.

Figure 3A:
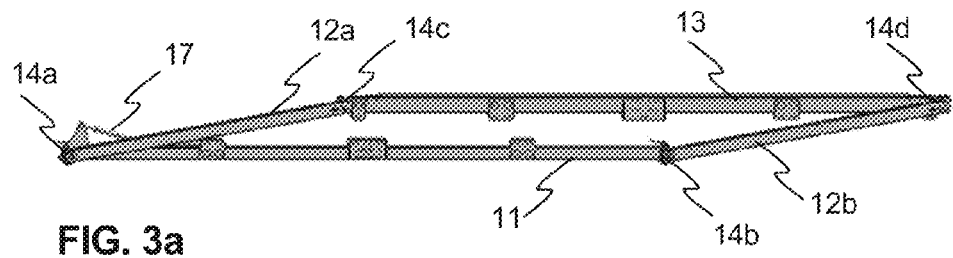
FIG. 3a illustrates an exemplary main frame in a collapsed position.
Figure 3B:
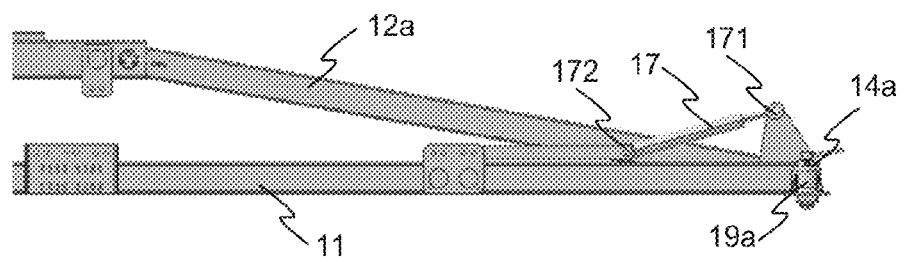
FIG. 3b illustrates an enlarged partial view of FIG. 3a showing the erecting equipment.

FIG. 3a illustrates a main frame in a collapsed position in which it is in an early stage of assembly. The main frame has articulated joints 14-14d at the corners in order to allow movement between collapsed and rectangular positions. The main frame has hydraulic means 17 for lifting the frame into rectangular position. The hydraulic means are attached to a lower horizontal beam 11 and one of the vertical beams 12 with articulated joints 171 and 172. FIG. 3b illustrates an enlarged partial figure of the hydraulic means.

Figure 4:
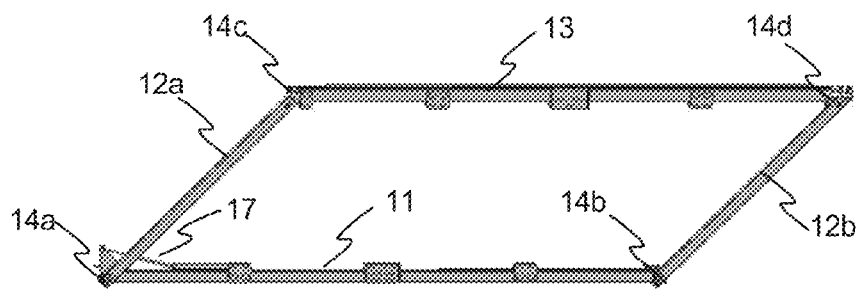
FIG. 4 illustrates an exemplary main frame when lifted into 45 degrees angle.
Figure 5A:
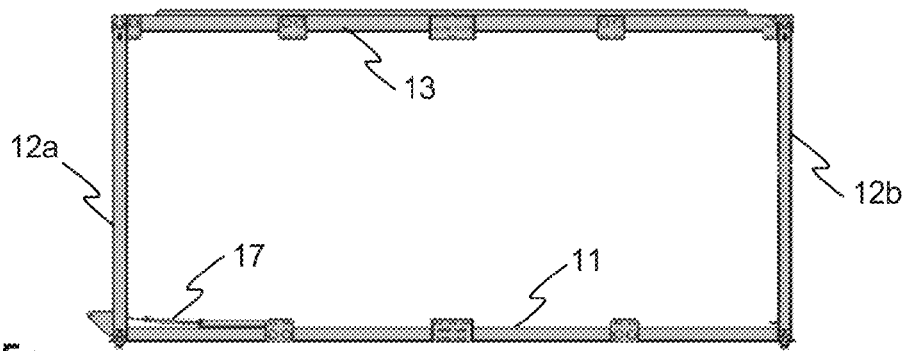
FIG. 5a illustrates an exemplary main frame in a final rectangular position with 90 degrees angle.
Figure 5B:
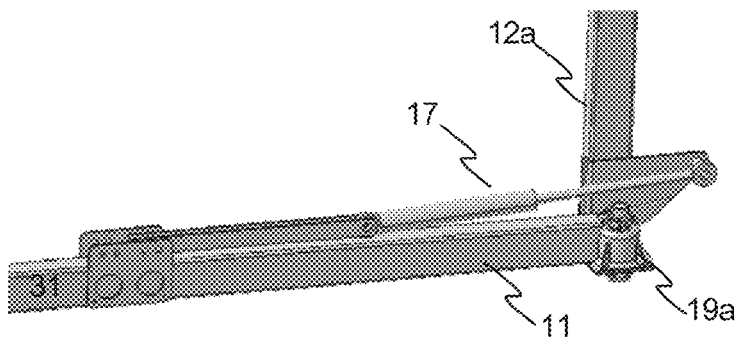
FIG. 5b illustrates an enlarged partial view of FIG. 5a showing the erecting equipment.

FIG. 4 illustrates the main frame in a position where it has been lifted into 45 degrees angle between horizontal and vertical support beams 11 and 12. FIG. 5a further illustrates the main frame when it has been lifted into final installation position of 90 degrees angle. FIG. 5b illustrates a partial enlarged figure of the hydraulic means 17 in the final position of the main frame.

Figure 6:
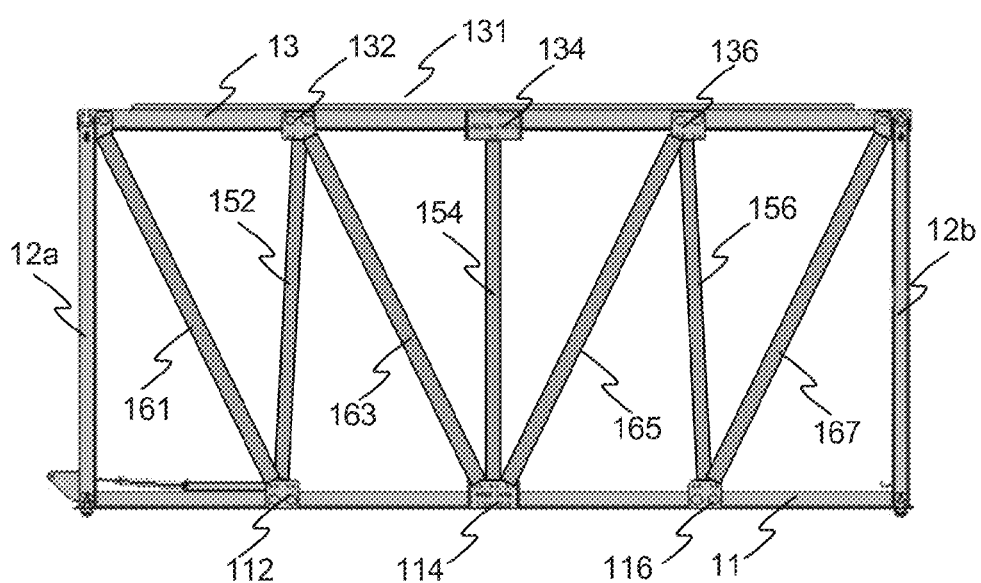
FIG. 6 illustrates an exemplary main frame with support beams installed.

FIG. 6 illustrates the main frame with support beams inside the rectangular main frame. The are substantially vertical support beams 152, 154 and 156, and diagonal support beams 161, 163, 165 and 167. The number and positions of the support beams may naturally be different than shown in the FIG. 6. The support beams are attached to the lower horizontal beam of the main frame at attachment points 112, 114 and 116. The support beams are respectively attached to the upper horizontal beam of the main frame at attachment points 132, 134 and 136.

Figure 7A:
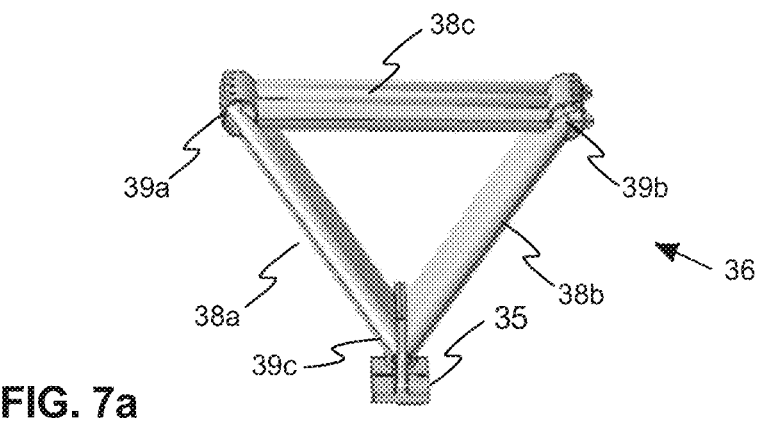
FIG. 7a illustrates an end view of an exemplary crane bridge.
Figure 7B:
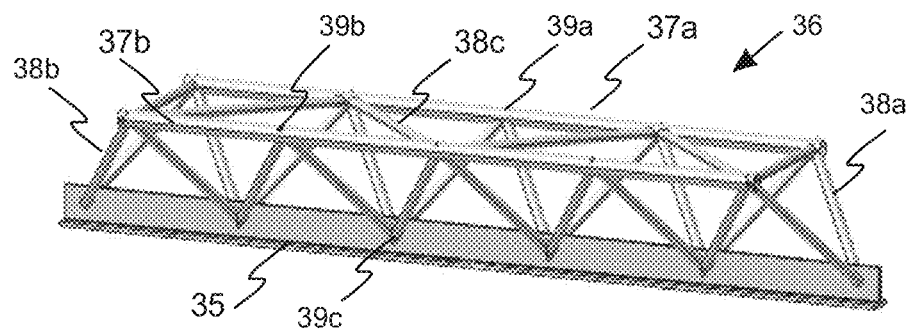
FIG. 7b illustrates a perspective view of an exemplary crane bridge.

FIG. 7a illustrates an end view of an exemplary crane bridge of the assembly, and FIG. 7b illustrates a perspective view of the same. The bridge has a beam profile 35 for carrying the hoist and allowing the movement of the hoist along the beam profile. There is also a support structure 36 for supporting the beam profile. The support structure comprises two longitudinal beams 37a and 37b. The longitudinal beams are fixed to each other with horizontal beams 38c. The longitudinal beams are further fixed to the beam profile 35 with diagonal beams 38a and 38b. The citations 39a, 39b and 39c illustrate the respective connection positions. The bridge profile is supported on the support frames 20 and 30 with movable trolleys 31 and 32 according to FIG. 1.

Figure 8:
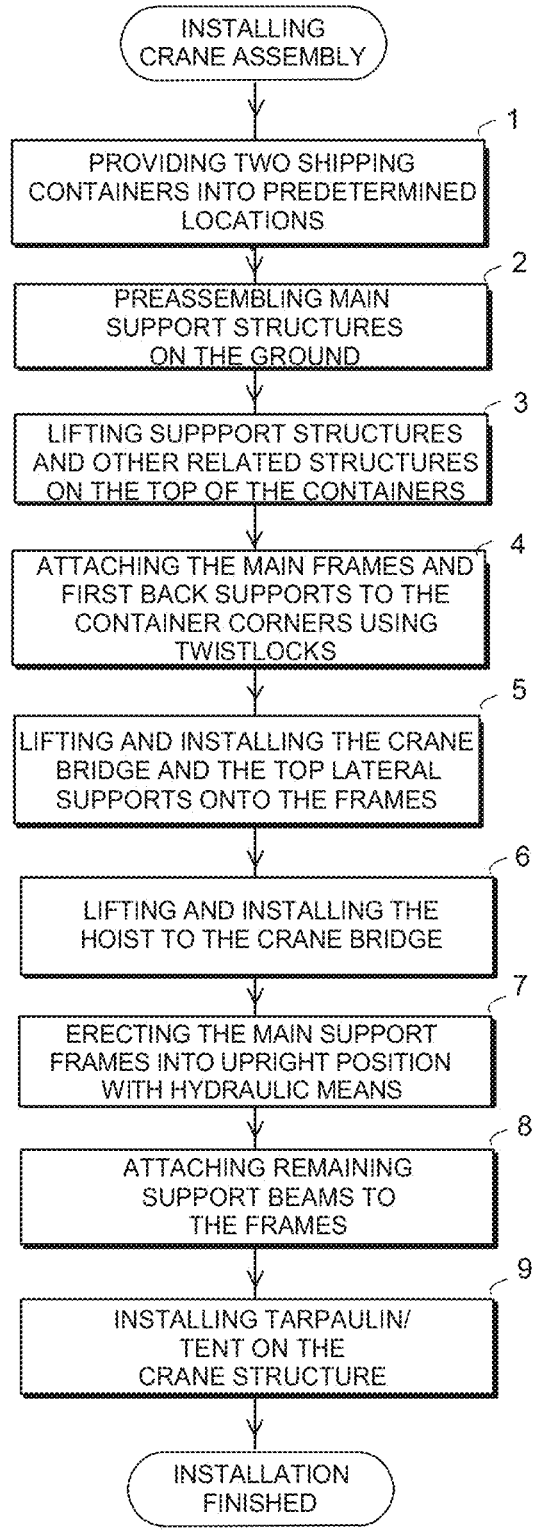
FIG. 8 illustrates a flow diagram of an exemplary method according to the invention for installing a bridge crane.

FIG. 8 illustrates a flow diagram of an exemplary method according to the invention for installing a bridge crane assembly. First in phase 1 two containers are provided. These are preferably standard shipping containers. Next in phase 2 main support structures are preassembled on ground. In phase 3 support structures and related parts are lifted on the top of the containers. In phase 4 the main frames are attached to the front top corners of the containers and the first back support beams 18a and 28a are attached between top corners of the main frame and the back top corners of the container. The attachment to the container is accomplished using twistlocks.

The crane bridge is then lifted and installed on the folded support frames in phase 5, and the hoist is lifted and installed on the carrier beam of the crane bridge in phase 6. An auxiliary crane can be used for lifting the parts of the bridge crane assembly as well as supporting the frame during the installation. In such case the auxiliary crane is first lifted on the top of each container consecutively. The auxiliary crane has its own, small hoist for lifting the frames, the crane bridge and other components.

The attached frames are then lifted from a collapsed position into final rectangular position, phase 7. This is preferably accomplished with hydraulic means that are integrated to the main frames. Support beams are next attached to the inside of the main frames in phase 8. These support beams lock the main frame into rectangular position and carry loads during the subsequent usage of the bridge crane. The remaining back support beams 18b and 28b are also attached to the upright frame in phase 8. The attachment to the container is accomplished using twist-locks. Finally in phase 9 it is possible to install a tent for covering the bridge crane assembly and for providing protection from environmental conditions.

Above some exemplary devices according to the invention have been described. The principle of the invention can naturally be modified within the scope of protection determined by the patent claims, e.g. in details of implementation and areas of use.

For example, the invention has significant advantages when used in crisis areas, but the invention is not in any way restricted to such use, and it can thus be applied in many other targets as well. The invention is applicable in military use, but it can also have has invention can be used in military applications, but it can also be used for other, peace time applications.

Above, certain order of installation phases is described. However, it should be noted that other alternative order of installation phases can be used.

The invention claimed is:

1. A bridge crane assembly, suitable for use in field conditions, such as crisis areas, comprising:
   first and second containers resting on a ground surface, the first and second containers being shipping containers, the first container being spaced apart from the second container with an ground surface region being located between corners of the first and second containers, and between longitudinal surfaces of the first and second containers;
   at least one horizontal crane bridge extending between the first and second containers and over the ground surface, the at least one horizontal crane bridge having a first end and an opposite, second end, the at least one crane bridge having a beam profile between the first and second ends;
   first and second support frame structures respectively that support the first and second ends of the at least one crane bridge; and
   a hoist that is carried by the at least one crane bridge in vertical alignment over the ground surface, the at least one crane bridge allowing movement of the hoist along the beam profile between the first and second ends of the at least one crane bridge in vertical alignment over the ground surface and between the first and second containers,
   wherein the first support frame structure comprises means for fixing the first support frame structure to the top of the first container and the second support frame structure comprises means for fixing the second support frame structure to the top of the second container, such that in use the first and second support frame structures are respectively fixed on the top of the first and second containers, the first and second support frame structures respectively support the first and second end of the at least one crane bridge, and the hoist is carried on the at least one crane bridge and positioned for lifting loads located on the ground surface region between the first and second containers, between the longitudinal surfaces of the first and second containers, and below the at least one crane bridge.

2. The bridge crane assembly according to claim 1, wherein the means for fixing the first support frame structure to the top of the first container and the means for fixing the second support frame structure to the top of the second container each comprise twistlocks.

3. The bridge crane assembly according to claim 1, wherein each of the first and second support frame structures comprise horizontal support beams supporting the at least one horizontal crane bridge, and wherein the at least one horizontal crane bridge is movable along said support beams.

4. The bridge crane assembly according to claim 1, wherein the at least one horizontal crane bridge, the first and second support frame structures, and the hoist fit inside the first and second containers.

5. The bridge crane assembly according to claim 1, further comprising hydraulic means for erecting the first and second supporting frame structures into a final upright position.

6. A method for installing a bridge crane, the method comprising:
   resting first and second containers on a ground surface with the first container being spaced apart from the second container to provide a ground surface region located between corners of the first and second containers, and between longitudinal surfaces of the first and second containers, the first and second containers being shipping containers,
   fixing a first support frame structure to a top corners of the first container,
   fixing a second support frame structure is fixed to a top corners of the second container,
   connecting a crane bridge with a beam profile is on and between the first and second support frame structures, and
   connecting a hoist to the crane bridge, wherein the beam profile carries the hoist and allows movement of the hoist along the beam profile for the hoist lifting loads located on the ground surface region in vertical alignment below at least one horizontal crane bridge and between the first and second containers, between the longitudinal surfaces of the first and second containers, and below the crane bridge.

7. The method according to the claim 6, wherein the first and second support frame structures are fixed to the top corners of the first and second containers with twistlocks.

8. The method according to claim 6, wherein an auxiliary crane is used in the installation for lifting and supporting parts on the first and second containers.

9. The method according to claim 6, wherein hydraulic erection equipment is used to erect the each supporting frame structure into a final upright position.

10. A bridge crane assembly, comprising:

a first container having a first door at one end;

a second container having a second door at one end, the first and second containers resting on a ground surface, the first and second containers being shipping containers, the first container being spaced apart from the second container with a ground surface region being located between corners the first and second containers;

collapsible first and second support frame structures erectable between an initial collapsed position and an upright final rectangular position, each of said first and second support frame structures having i) a main frame comprised of horizontal lower beam, a horizontal upper beam, two vertical beams connecting the horizontal upper and lower beams to each other, and attachment parts that attach the main frame to a top of one of the first and second containers, and ii) support beams and diagonal support beams that, with the main frame in the final rectangular position, extend between the horizontal upper and lower beams;

a horizontal crane bridge having a first end and an opposite, second end, the crane bridge having a beam profile between the first and second ends, wherein with the main frame in the final rectangular position and the first and second support frame structures fixed to the tops of the first and second containers, the first and second support frame structures respectively support the first and second ends of the crane bridge spanning, in vertical alignment, over the ground surface region and between the tops of the first and second containers; and a hoist carried by the beam profile of the crane bridge, the hoist being moveable, in vertical alignment, over and between the tops of the first and second containers along the beam profile between the first and second ends of the crane bridge, wherein, in use with the first and second support frame structures respectively fixed on the top of the first and second containers, the first and second support frame structures respectively supporting the first and second end of the crane bridge, and the hoist being carried on the crane bridge, the hoist is positioned for lifting loads located on the ground surface region in vertical alignment below the at least one horizontal crane bridge and between the first and second containers and below the crane bridge, and between the longitudinal surfaces of the first and second containers.

11. The bridge crane assembly according to claim 10, wherein the attachment parts are twistlocks.

12. The bridge crane assembly according to claim 10, wherein the crane bridge is movable along said horizontal upper beams of the first and second support frame structures.

13. The bridge crane assembly according to claim 10, further comprising top lateral supports that tie together the horizontal upper beams of the first and second support frame structures.

14. The bridge crane assembly according to claim 10, wherein the horizontal upper beams of the first and second support frame structures respectively fit inside the first and second containers.

15. The bridge crane assembly according to claim 10, further comprising hydraulic means for erecting the first and second supporting frame structures into the upright final rectangular position.

\* \* \* \* \*